(12) United States Patent
Jenkins

(10) Patent No.: US 9,066,724 B2
(45) Date of Patent: Jun. 30, 2015

(54) SURGICAL INSTRUMENT

(75) Inventor: Andrew Edward Jenkins, Rhondda Cynon Taff (GB)

(73) Assignee: GYRUS MEDICAL LIMITED, Cardiff (GB)

( * ) Notice: Subject to any disclaimer, the term of this patent is extended or adjusted under 35 U.S.C. 154(b) by 1050 days.

(21) Appl. No.: 13/086,696

(22) Filed: Apr. 14, 2011

(65) Prior Publication Data

US 2011/0257651 A1 Oct. 20, 2011

(30) Foreign Application Priority Data

Apr. 15, 2010 (GB) .................................. 1006320.4

(51) Int. Cl.
| | |
|---|---|
| *A61B 18/18* | (2006.01) |
| *A61B 18/14* | (2006.01) |
| *A61B 17/32* | (2006.01) |
| *A61B 18/00* | (2006.01) |
| *A61B 18/16* | (2006.01) |

(52) U.S. Cl.
CPC . *A61B 18/1485* (2013.01); *A61B 2017/320024* (2013.01); *A61B 2018/00559* (2013.01); *A61B 2018/00601* (2013.01); *A61B 2018/162* (2013.01)

(58) Field of Classification Search
CPC ..................... A61B 18/1485; A61B 2018/162; A61B 2018/006; A61B 2017/320024; A61B 2018/00559
USPC ...................................................... 606/48, 50
See application file for complete search history.

(56) References Cited

U.S. PATENT DOCUMENTS

| | | | |
|---|---|---|---|
| 6,007,512 A | 12/1999 | Hooven | |
| 6,395,002 B1 | 5/2002 | Ellman et al. | |
| 6,676,659 B2 * | 1/2004 | Hutchins et al. | ................. 606/47 |

(Continued)

FOREIGN PATENT DOCUMENTS

| | | |
|---|---|---|
| GB | 2414185 | 11/2005 |
| GB | 2 436 065 | 9/2007 |

(Continued)

OTHER PUBLICATIONS

UK Search Report for Application No. GB30906573.1, dated Jul. 23, 2009.

(Continued)

*Primary Examiner* — Joseph Stoklosa
*Assistant Examiner* — Eunhwa Kim
(74) *Attorney, Agent, or Firm* — Nixon & Vanderhye PC

(57) ABSTRACT

A device for morcellating tissue within a body cavity of a patient comprises a stationary tube (8) having a distal end portion, and a bipolar electrosurgical electrode assembly (13) located at the distal end of the tube. The electrosurgical electrode assembly (13) comprises first and second electrodes (14, 16) separated by an insulation member (15). When an electrosurgical cutting voltage is applied to the electrode assembly (13), and relative movement is initiated between the tube (8) and the tissue, a slug of severed tissue is formed within the tube such that it can be removed from the body cavity of the patient. The bipolar electrosurgical assembly (13) has a first circumferential region (A) and a second circumferential region (B), the first circumferential region (A) being longer than the second circumferential region (B). In the first circumferential region (A), the first electrode (14) is disposed further forwardly as compared with the second electrode (16); and, in the second circumferential region (B), the second electrode (16) is disposed at least as far forwardly as compared with the first electrode (14).

5 Claims, 2 Drawing Sheets

(56) References Cited

U.S. PATENT DOCUMENTS

| | | |
|---|---|---|
| 7,232,439 B2 * | 6/2007 | Ciarrocca .................. 606/48 |
| 2005/0070892 A1 | 3/2005 | Ciarrocca |
| 2005/0261677 A1 * | 11/2005 | Hall et al. .................. 606/48 |
| 2006/0178670 A1 * | 8/2006 | Woloszko et al. .......... 606/48 |
| 2008/0039883 A1 | 2/2008 | Nohilly |
| 2009/0018540 A1 | 1/2009 | Eitenmueller |
| 2009/0292281 A1 * | 11/2009 | Fleming et al. ............ 606/48 |

FOREIGN PATENT DOCUMENTS

| | | |
|---|---|---|
| GB | 2460242 | 11/2009 |
| WO | WO 94/00060 | 1/1994 |
| WO | WO 96/24296 | 8/1996 |
| WO | WO 2005/112806 | 12/2005 |
| WO | WO 2010/119238 | 10/2010 |

OTHER PUBLICATIONS

International Search Report for corresponding International Appl. No. PCT/GB2011/000524, mailed Jun. 8, 2011.

Written Opinion of Searching Authority for corresponding International Appl. No. PCT/GB2011/000524, mailed Jun. 8, 2011.

Search Report issued in corresponding UK Application No. GB1006320.4, Date of Search: Jul. 22, 2011.

* cited by examiner

SURGICAL INSTRUMENT

TECHNICAL FIELD

This invention relates to a bipolar electrosurgical instrument for use in the bulk removal of tissue, as in a laparoscopic hysterectomy.

BACKGROUND TO THE INVENTION

In a laparoscopic hysterectomy, the body of the uterus is resected from the stump or fundus, and then removed from the operative site. To enable the uterus to be removed through a limited surgical opening, it is desirable to morcellate it into relatively smaller pieces of tissue, which are easier to remove. Our pending patent application, published as WO05/112806 describes an electrosurgical morcellator for the bulk removal of tissue. The present invention relates to an improvement to this type of instrument.

In the device of WO05/112806, a bipolar electrosurgical cutting assembly is provided at the distal end of a tube. The electrosurgical cutting assembly cuts tissue effectively provided that the tissue is in contact with both electrodes. However, as the tissue is cut and a slug of tissue enters the tube, the tissue can become separated from the return electrode making further cutting ineffective. The device of WO05/112806, therefore, has a tissue-grasping instrument connected to the electrosurgical generator, in order to provide an additional return electrode that remains in contact with the tissue as it is drawn into the tube.

While this arrangement works well enough, the connection of the tissue-grasping instrument to the generator does have certain drawbacks. It requires an additional lead to be present between the instrument and the generator, adding to the difficulty in manipulating the instrument. Furthermore, the tissue grasping instrument needs to be provided with a bespoke connector, and this means that the user is not able to use a generic tissue grasper, even if this is preferred.

SUMMARY OF INVENTION

The present invention attempts to avoid these minor problems by dispensing with the need for the tissue-grasping instrument to be connected to the electrosurgical generator, while ensuring that effective tissue cutting still occurs.

Accordingly, a device for morcellating tissue within a body cavity of a patient is provided, the morcellating device comprising a stationary tube having a distal end portion, the distal end portion including a bipolar electrosurgical electrode assembly including first and second electrodes located at the distal end of the tube and separated one from the other by an insulation member, the first electrode constituting an active cutting electrode, and the second electrode constituting a return electrode, the morcellating device having a first circumferential region and a second circumferential region, the first circumferential region being longer than the second circumferential region, the first electrode being disposed further forwardly as compared with the second electrode in the first circumferential region, and the second electrode being disposed at least as far forwardly as compared with the first electrode in the second circumferential region, the arrangement being such that, when an electrosurgical cutting voltage is applied to the electrode assembly, tissue can be pulled against the distal end of the tube to form a slug of severed tissue within the tube, and, in the second circumferential region, the second electrode remains in contact with the unsevered tissue within the body cavity.

By providing a second circumferential region in which the second electrode is disposed at least as far forwardly as compared with the first electrode, contact between the second electrode and the tissue is encouraged, even when tissue is being drawn into the tube. In a convenient arrangement, the second electrode is disposed further forwardly as compared with the first electrode in the second circumferential region.

One effect of providing the second circumferential region in which the second electrode extends forwardly further than the first electrode is that electrosurgical cutting of tissue directly in the second circumferential region is less likely to take place. However, as long as the second circumferential region is not an excessive proportion of the overall circumference of the tube, this will not be a problem, and may even be an advantage. By providing an electrosurgical cutting assembly in which the cutting instrument is unable to cut around the whole of the 360° circumference of the tube, the cutting tip is less likely to be able to remove a core of tissue and become buried within the body of the organ being morcellated. With a section of the tissue being less easily cut, the morcellating instrument removes tissue at the surface of the organ in a more controlled peeling action. However, this "anti-coring" effect is only an additional advantage of the present invention. The main advantage is the improved tissue contact with the return electrode as discussed above, removing any requirement for a tissue grasper to be electrically connected to the electrosurgical generator.

The second circumferential region should not be so great as to substantially affect the cutting capability of the instrument, and so the first circumferential region extends around more than 50% of the circumference of the tube, and preferably around at least 80% of the tube. Convenient arrangements have the second circumferential region constituting approximately 33%, 20% or even 10% of the circumference of the tube.

To provide the contact with the tissue, the second electrode conveniently includes an extension that overlies the first electrode in the second circumferential region. In one arrangement, this extension is folded over the first electrode in the second circumferential region so as to mask the first electrode and contact the tissue in its place. The extension is preferably integrally formed with the remainder of the second electrode. The second electrode is conveniently disposed around the inside of the tube. In this way, it continues to make contact with tissue as it is drawn into the tube.

In one conceivable arrangement, the second circumferential region is selectively rotatable around the circumference of the morcellating device by the user of the instrument. In this way, the user of the instrument can vary the position of the second circumferential region at will. The tube is preferably provided with a marker in alignment with the second circumferential region, so that the user can easily determine the orientation of the second circumferential region with respect to the device as a whole.

DESCRIPTION OF THE DRAWINGS

The invention will now be described in more detail, by way of example, with reference to the drawings, in which.

DESCRIPTION OF THE EMBODIMENTS

Figure 1:
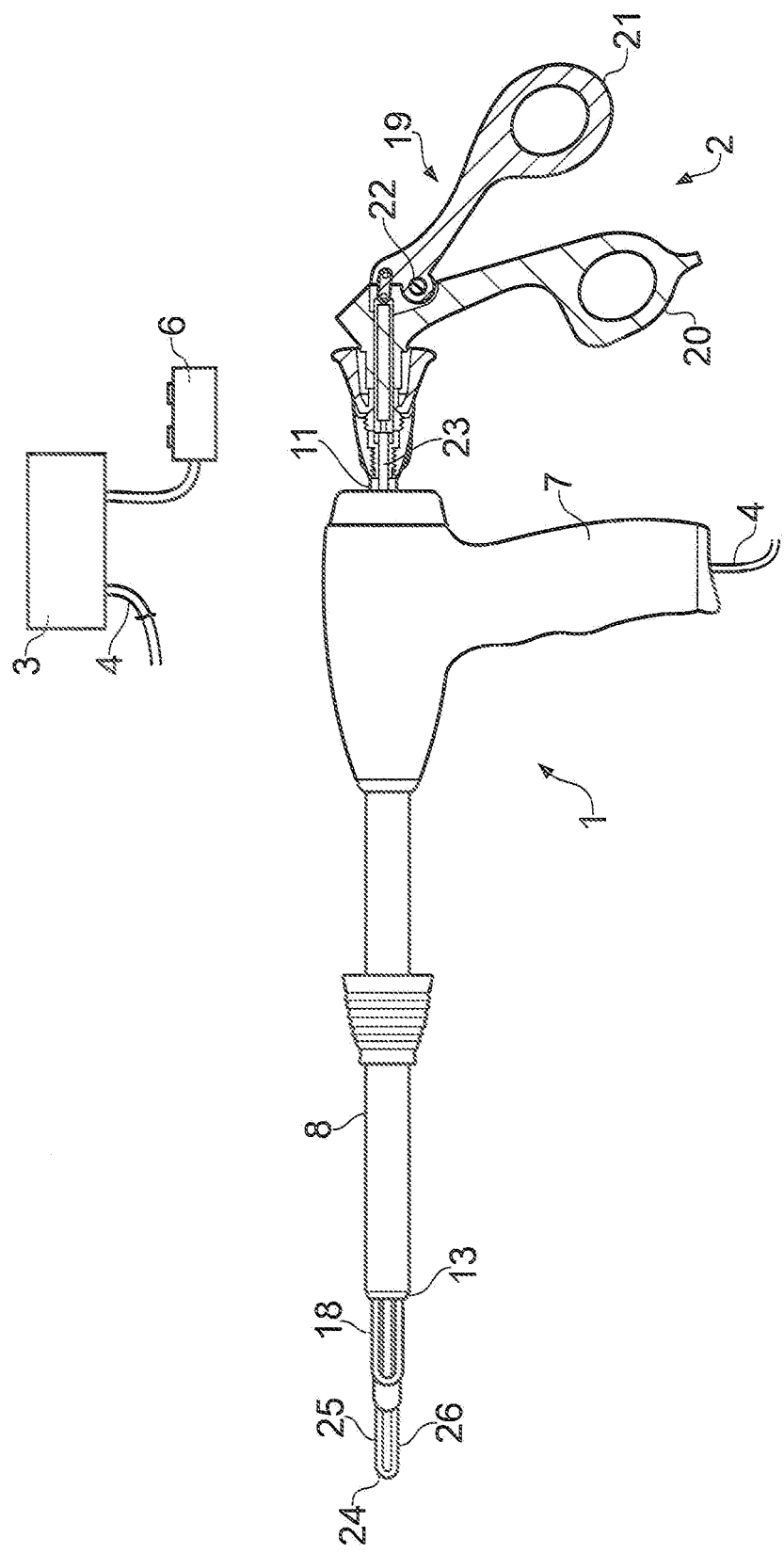
FIG. 1 is a schematic side view, partly in section, of a morcellating device connected in accordance with the invention.

Referring to FIG. 1, a morcellating system comprises a morcellating device shown generally at 1, a tissue-pulling device shown generally at 2, and an electrosurgical generator 3. The generator 3 is connected to the morcellating device 1 by means of a cable 4, and is controlled by means of a footswitch 6.

Figure 2:
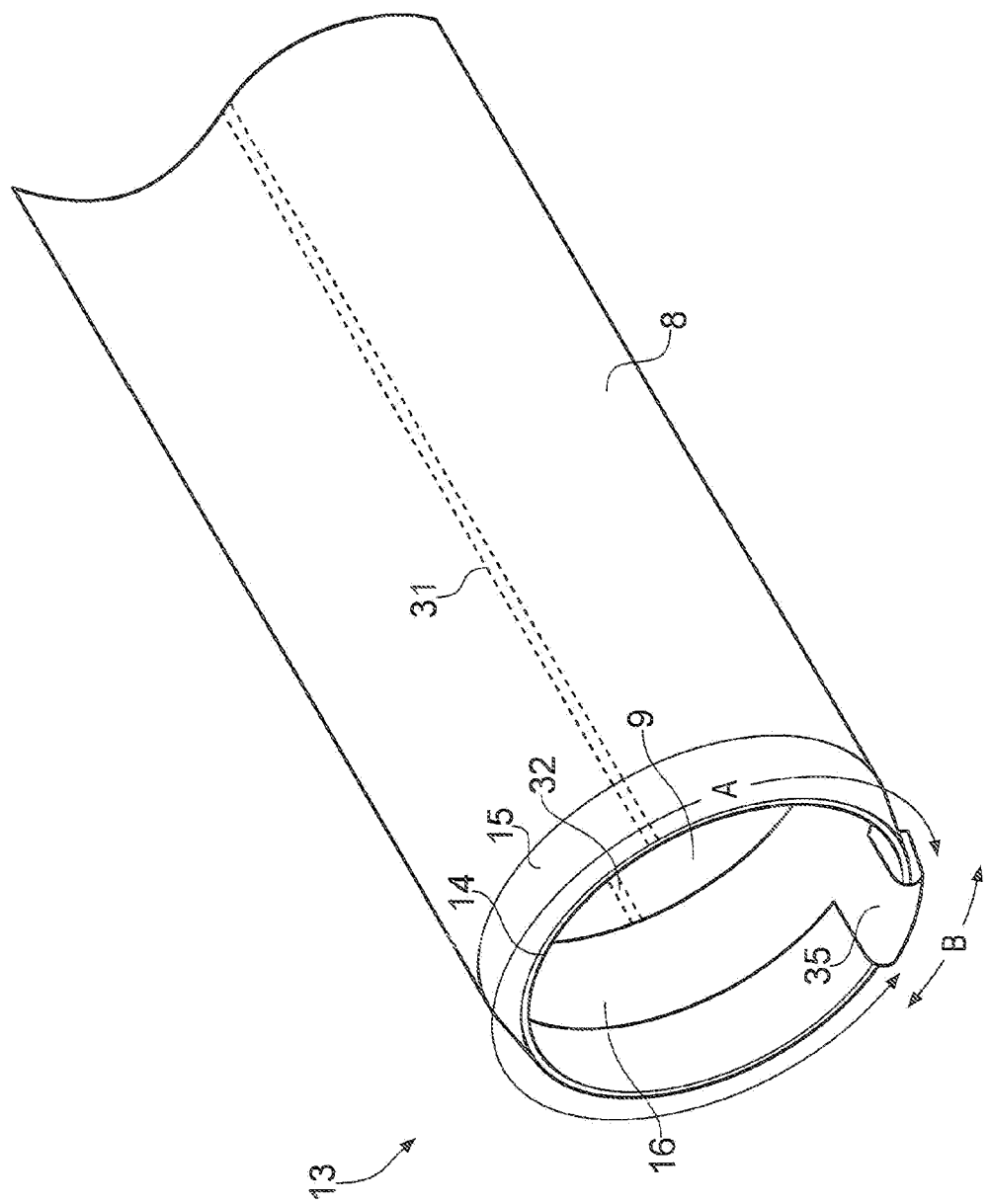
FIG. 2 is an enlarged view of a part of the device shown in FIG. 1.

As shown in FIGS. 1 and 2, the morcellating device 1 comprises a handle 7 and a cylindrical tube 8. The cylindrical tube 8 is hollow, and defines a lumen 9 therein. The proximal end of the tube 8 extends from the handle 7 as shown at 11, and the distal end of the tube is provided with an electrosurgical electrode assembly 13. The electrosurgical electrode assembly 13 comprises an active tissue-cutting electrode 14, and an insulation member 15, both extending around the circumference of the tube 8. The insulation member 15 separates the electrode 14 from a return electrode 16, also located on the tube 8.

The active electrode 14 extends around the circumference of the tube 8, and is connected to one pole of the generator 3, via a lead 31 and the cable 4. The return electrode 16 is connected to the other pole of the generator 3, via a lead 32 and the cable 4. In this way, the electrodes 14 and 16 constitute a bipolar electrode assembly, which, when energised by the generator 3, is capable of cutting tissue coming into contact with the distal end of the tube 8.

The tissue-pulling device 2 comprises a tubular shaft 18, at the proximal end of which is a scissors-type handle mechanism 19, having a first handle 20 and a second handle 21. The second handle 21 is pivotable with respect to the first handle 20, about a pivot pin 22. Pivoting of the second handle 21 causes longitudinal movement of a push rod 23 extending through the shaft 18 to the distal end thereof.

At the distal end of the shaft 18 is a jaw assembly 24, with a first jaw member 25 and a second jaw member 26 movable between open and closed positions by the movement of the push rod 23. The tissue-pulling device 2 is manually translatable in a longitudinal manner within the lumen 9 of the morcellating device 1.

The operation of the morcellating system is as follows. The tube 8 of the morcellating device 1 is inserted into the body of a patient, typically through a trocar (not shown), or optionally directly into an incision made in the body of the patient. The device 1 is brought into position adjacent to the tissue to be removed, which is typically a resected uterus in the case of a laparoscopic hysterectomy. The tissue-pulling device 2 is then inserted through the lumen 9 of the morcellating device 1. The handle 21 is operated to open the jaw assembly 24, and the tissue-pulling device 2 is manoeuvred so that tissue from the uterus is located between the jaw members 25 and 26. The handle 21 is then operated to close the jaw assembly 24, grasping tissue therein.

The surgeon operates the footswitch 6 to operate the generator 3 so that an electrosurgical cutting voltage is supplied between the active electrode 14 and the return electrode 16. With tissue firmly grasped in the jaw assembly 24, the device 2 is slowly withdrawn from the tube 8, pulling the tissue against the distal end of the tube and the active electrode 14. As the tissue contacts the active electrode 14, it is vaporised, allowing the device 2 to be withdrawn further into the tube 8. In this way, a cylindrical slug of tissue is formed in the tube 8, the tissue being withdrawn though the proximal end of the morcellating device 1 (which remains outside the body of the patient) for disposal.

The tissue-pulling device 2 can then be re-inserted into the tube 8 such that a further slug of tissue can be removed from the body of the patient. By repeating this process, large quantities of tissue can be removed from the patient in a relatively short time, such that the entire uterus can be removed, if necessary, while still employing a laparoscopic approach.

FIG. 2 shows the distal end of the tube 8 in which the active electrode 14 extends around the circumference of the tube in a first circumferential region A. The return electrode 16 extends completely around the tube 8 as shown, and is provided with an extension 35 in a second circumferential region B. In the second circumferential region B the extension 35 overlies the active electrode 14, and is folded over the active electrode 14 to mask it from tissue. Additional insulation members (not shown) ensure that there is no direct contact between the extension 35 and the active electrode 14. The first circumferential region A may extend around at least 80% of the circumference of the tube 8.

When the electrosurgical cutting voltage is supplied between the electrodes 14 and 16, and tissue is pulled against the electrodes by the tissue-pulling device 2, the tissue will be electrosurgically cut in the region A, but remain unsevered in the region B. More and more tissue can be pulled against the tube 8 by the retraction of the tissue-pulling device 2, and the result will be a peeling of tissue with a segment of the tissue remaining connected to the uterus adjacent to the region B. In this way, the tube 8 will remain towards the edge of the uterus, rather than being buried into the tissue to produce a coring action.

The extension 35 will ensure that the return electrode 16 remains in contact with tissue even when slugs of tissue are being pulled into the tube. The extension provides a forwards portion of the return electrode 16 even though it is the active electrode 14 that is located forwardly over the majority of the circumference of the tube 8.

Those skilled in the art will appreciate that other arrangements can be envisaged in which a portion of the return electrode 16 is disposed either forwardly of the active electrode 14, or at least flush with the active electrode. Conceivably, the extension 35 can be longitudinally deployable, so as to vary the extent to which it extends forwardly. In this way, the user can adjust the extension to ensure the correct contact with the unsevered tissue. The tube 8 could also be provided with a marker in alignment with the second circumferential region B, so as to highlight the position of that region to a user of the device.

Additionally, if the user of the instrument does not wish to change the orientation of the device as a whole by rotating iten masse, the electrosurgical assembly 13 can be designed so as to be rotatable with respect to the tube 8, for example by means of a collar (not shown). Alternatively, just the return electrode 16, or even just the extension 35, can be made rotatable. There are also alternatives to having the extension 35 folded over the active electrode 14. An example of an alternative arrangement within the scope of the present invention is to have the active electrode 14 extend only around the circumferential region A, and not to extend into the circumferential region B. In this way the extension 35 can easily be made to be flush with the active electrode 14, with the active and return electrodes being circumferentially separated by insulating spacers (not shown). These and other alternative arrangements are readily available without departing from the scope of the present invention.

The invention claimed is:

1. A device for morcellating tissue within a body cavity of a patient, the morcellating device comprising:
   a stationary tube having a distal end portion,
   the distal end portion including a bipolar electrosurgical electrode assembly including first and second electrodes located at the distal end of the tube and separated one from the other by an insulation member,
   the first electrode constituting an active cutting electrode, and the second electrode constituting a return electrode, the morcellating device having a first circumferential region and a second circumferential region, the first circumferential region being longer than the second circumferential region, the first electrode being disposed further forwardly as compared with the second electrode in the first circumferential region, and the second electrode being disposed at least as far forwardly as compared with the first electrode in the second circumferential region, the arrangement being such that, when an electrosurgical cutting voltage is applied to the electrode assembly, tissue can be pulled against the distal end of the tube to form a slug of severed tissue within the tube, and, in the second circumferential region, the second electrode being adapted to remain in contact with tissue within the body cavity that is other than the severed tissue within the tube, wherein the second electrode is disposed further forwardly as compared with the first electrode in the second circumferential region, wherein the second electrode includes an extension that overlies the first electrode in the second circumferential region, and wherein the extension is folded over the first electrode in the second circumferential region.

2. The morcellating device according to claim 1, wherein the extension is integrally formed with the remainder of the second electrode.

3. The morcellating device according to claim 1, wherein the second electrode is disposed around the inside of the tube.

4. The morcellating device according to claim 1, wherein the first circumferential region extends around at least 80% of the circumference of the tube.

5. A device for morcellating tissue within a body cavity of a patient, the morcellating device comprising:

a stationary tube having a distal end portion, the distal end portion including a bipolar electrosurgical electrode assembly including first and second electrodes located at the distal end of the tube and separated one from the other by an insulation member, the first electrode constituting an active cutting electrode, and the second electrode constituting a return electrode, the morcellating device having a first circumferential region and a second circumferential region, the first circumferential region being longer than the second circumferential region, the first electrode being disposed further forwardly as compared with the second electrode in the first circumferential region, and the second electrode being disposed at least as far forwardly as compared with the first electrode in the second circumferential region, the arrangement being such that, when an electrosurgical cutting voltage is applied to the electrode assembly, tissue can be pulled against the distal end of the tube to form a slug of severed tissue within the tube, and, in the second circumferential region, the second electrode being adapted to remain in contact with tissue within the body cavity that is other than the severed tissue within the tube, and wherein the second circumferential region is selectively rotatable around the circumference of the morcellating device by the user of the instrument.

* * * * *